(12) United States Patent
Culbert

(10) Patent No.: US 9,408,648 B2
(45) Date of Patent: Aug. 9, 2016

(54) METHOD AND APPARATUS FOR BONE FIXATION WITH SECONDARY COMPRESSION

(71) Applicant: Interventional Spine, Inc., Irvine, CA (US)

(72) Inventor: Brad S. Culbert, Rancho Santa Margarita, CA (US)

(73) Assignee: Interventional Spine, Inc., Irvine, CA (US)

( * ) Notice: Subject to any disclaimer, the term of this patent is extended or adjusted under 35 U.S.C. 154(b) by 0 days.

(21) Appl. No.: 14/216,400

(22) Filed: Mar. 17, 2014

(65) Prior Publication Data

US 2015/0018891 A1 Jan. 15, 2015

Related U.S. Application Data

(60) Continuation of application No. 11/050,966, filed on Feb. 4, 2005, now Pat. No. 8,715,284, which is a division of application No. 10/195,832, filed on Jul. 12, 2002, now Pat. No. 6,887,243, which is a continuation-in-part of application No. 09/991,367, filed on Nov. 13, 2001, now Pat. No. 6,890,333, which is a continuation-in-part of application No. 09/822,803, filed on Mar. 30, 2001, now Pat. No. 6,511,481.

(51) Int. Cl.

| A61B 17/16 | (2006.01) |
|---|---|
| A61B 17/84 | (2006.01) |
| A61B 17/68 | (2006.01) |
| A61B 17/74 | (2006.01) |
| A61B 17/86 | (2006.01) |

(52) U.S. Cl.
CPC .............. *A61B 17/846* (2013.01); *A61B 17/68* (2013.01); *A61B 17/742* (2013.01); *A61B 17/16* (2013.01); *A61B 17/1615* (2013.01); *A61B 17/744* (2013.01); *A61B 17/864* (2013.01); *A61B 17/869* (2013.01); *A61B 17/8685* (2013.01)

(58) Field of Classification Search
CPC .............. A61B 17/72; A61B 17/7208; A61B 17/7216; A61B 17/7233; A61B 17/7283; A61B 17/7291; A61B 17/74; A61B 17/742; A61B 17/744; A61B 17/746; A61B 17/748; A61B 17/16; A61B 17/1615; A61B 17/864
USPC ............................... 606/300–331, 105, 65–68
See application file for complete search history.

(56) References Cited

U.S. PATENT DOCUMENTS

| 1,802,560 A | 4/1923 | Kerwin |
|---|---|---|
| 2,077,804 A | 4/1937 | Morrison |

(Continued)

FOREIGN PATENT DOCUMENTS

| CN | 1177918 | 4/1998 |
|---|---|---|
| DE | 198 32 798 | 11/1999 |

(Continued)

*Primary Examiner* — Mary Hoffman
(74) *Attorney, Agent, or Firm* — Knobbe, Martens, Olson & Bear, LLP

(57) ABSTRACT

Disclosed is a fracture fixation device, for reducing and compressing fractures in a bone. The fixation device includes an elongate body. An axially moveable proximal anchor is carried by the proximal end of the fixation device and comprises a tubular sleeve that includes a plurality of graduations positioned on an outer surface of the tubular sleeve. The device is rotated into position across the femoral neck and into the femoral head, and the proximal anchor is distally advanced to lock the device into place. In certain embodiments, the elongated body includes a distal anchor with a distal cutting tip.

7 Claims, 11 Drawing Sheets

(56) References Cited

U.S. PATENT DOCUMENTS

| | | | |
|---|---|---|---|
| 2,121,193 A * | 6/1938 | Hanicke | 606/65 |
| 2,388,056 A | 7/1943 | Hendricks | |
| 2,485,531 A | 10/1949 | Dzus et al. | |
| 2,489,870 A | 11/1949 | Dzus | |
| 2,570,465 A | 10/1951 | Lundholm | |
| 3,115,804 A | 12/1963 | Johnson | |
| 3,489,143 A | 1/1970 | Holloran | |
| 3,842,825 A | 10/1974 | Wagner | |
| 4,052,988 A | 10/1977 | Doddi et al. | |
| 4,175,555 A | 11/1979 | Herbert | |
| 4,262,665 A | 4/1981 | Roalstad et al. | |
| 4,275,717 A | 6/1981 | Bolesky | |
| 4,341,206 A | 7/1982 | Perrett et al. | |
| 4,456,005 A | 6/1984 | Lichty | |
| 4,463,753 A | 8/1984 | Gustilo | |
| 4,488,543 A | 12/1984 | Tornier | |
| 4,532,660 A | 8/1985 | Field | |
| 4,537,185 A | 8/1985 | Stednitz | |
| 2,173,655 A | 10/1986 | Himoud | |
| 4,632,101 A | 12/1986 | Freedland | |
| 4,640,271 A * | 2/1987 | Lower | 606/65 |
| 4,641,640 A | 2/1987 | Griggs | |
| 4,667,663 A | 5/1987 | Miyata | |
| 4,688,561 A | 8/1987 | Reese | |
| 4,721,103 A | 1/1988 | Freedland | |
| 4,743,257 A | 5/1988 | Tormala et al. | |
| 4,760,843 A | 8/1988 | Fischer et al. | |
| 4,790,304 A | 12/1988 | Rosenberg | |
| 4,796,612 A | 1/1989 | Reese | |
| 4,815,909 A | 3/1989 | Simons | |
| 4,827,917 A | 5/1989 | Brumfield | |
| 4,858,601 A | 8/1989 | Glisson | |
| 4,873,976 A | 10/1989 | Schreiber | |
| 4,898,186 A | 2/1990 | Ikada et al. | |
| 4,903,692 A | 2/1990 | Reese | |
| 4,917,554 A | 4/1990 | Bronn | |
| 4,927,421 A * | 5/1990 | Goble et al. | 606/232 |
| 4,940,467 A * | 7/1990 | Tronzo | 606/66 |
| 4,959,064 A | 9/1990 | Engelhardt | |
| 4,963,144 A | 10/1990 | Huene | |
| 4,968,317 A | 11/1990 | Tormala et al. | |
| 4,978,349 A | 12/1990 | Frigg | |
| 4,988,351 A | 1/1991 | Paulos et al. | |
| 5,013,315 A | 5/1991 | Barrows | |
| 5,013,316 A | 5/1991 | Goble et al. | |
| 5,059,193 A | 10/1991 | Kuslich | |
| 5,062,849 A | 11/1991 | Schelhas | |
| 5,092,891 A | 3/1992 | Kummer et al. | |
| 5,098,241 A | 3/1992 | Aldridge et al. | |
| 5,098,433 A | 3/1992 | Freedland | |
| 5,098,435 A | 3/1992 | Stednitz et al. | |
| 5,116,336 A | 5/1992 | Frigg | |
| 5,120,171 A | 6/1992 | Lasner | |
| 5,122,133 A | 6/1992 | Evans | |
| 5,122,141 A | 6/1992 | Simpson et al. | |
| 5,167,663 A | 12/1992 | Brumfield | |
| 5,167,664 A | 12/1992 | Hodorek | |
| 5,217,462 A | 6/1993 | Asnis et al. | |
| 5,234,431 A | 8/1993 | Keller | |
| 5,242,447 A | 9/1993 | Borzone | |
| 5,246,441 A | 9/1993 | Ross et al. | |
| 5,250,049 A | 10/1993 | Michael | |
| 5,300,074 A | 4/1994 | Frigg | |
| 5,312,410 A | 5/1994 | Miller et al. | |
| 5,334,184 A | 8/1994 | Bimman | |
| 5,334,204 A | 8/1994 | Clewett et al. | |
| 5,364,398 A | 11/1994 | Chapman et al. | |
| 5,370,646 A | 12/1994 | Reese et al. | |
| 5,370,661 A | 12/1994 | Branch | |
| 5,382,248 A | 1/1995 | Jacobson et al. | |
| 5,387,213 A | 2/1995 | Breard et al. | |
| 5,415,661 A | 5/1995 | Holmes | |
| 5,449,359 A | 9/1995 | Groiso | |
| 5,449,361 A | 9/1995 | Preissmann | |
| 5,452,748 A | 9/1995 | Simmons et al. | |
| 5,464,427 A | 11/1995 | Curtis et al. | |
| 5,470,333 A | 11/1995 | Ray | |
| 5,496,318 A | 3/1996 | Howland et al. | |
| 5,498,265 A | 3/1996 | Asnis et al. | |
| 5,501,695 A | 3/1996 | Anspach, Jr. et al. | |
| 5,520,690 A | 5/1996 | Errico et al. | |
| 5,527,312 A | 6/1996 | Ray | |
| 5,536,127 A | 7/1996 | Pennig | |
| 5,540,688 A | 7/1996 | Navas | |
| 5,545,164 A | 8/1996 | Howland | |
| 5,549,610 A | 8/1996 | Russell et al. | |
| 5,558,674 A | 9/1996 | Heggeness et al. | |
| D374,287 S | 10/1996 | Goble et al. | |
| 5,569,248 A | 10/1996 | Mathews | |
| 5,569,251 A | 10/1996 | Baker et al. | |
| 5,569,548 A | 10/1996 | Koike et al. | |
| 5,591,168 A | 1/1997 | Judet et al. | |
| 5,609,634 A | 3/1997 | Voydeville | |
| 5,618,142 A | 4/1997 | Sonden et al. | |
| 5,618,314 A | 4/1997 | Harwin et al. | |
| 5,626,613 A | 5/1997 | Schmieding | |
| 5,628,751 A | 5/1997 | Sander et al. | |
| 5,643,320 A | 7/1997 | Lower et al. | |
| 5,645,599 A | 7/1997 | Samani | |
| 5,649,931 A | 7/1997 | Bryant et al. | |
| 5,662,683 A | 9/1997 | Kay | |
| 5,667,508 A | 9/1997 | Errico et al. | |
| 5,669,915 A | 9/1997 | Caspar et al. | |
| 5,713,903 A | 2/1998 | Sander et al. | |
| 5,720,753 A | 2/1998 | Sander et al. | |
| 5,725,541 A | 3/1998 | Anspach, III et al. | |
| 5,725,588 A | 3/1998 | Errico et al. | |
| 5,728,097 A | 3/1998 | Mathews | |
| 5,728,116 A | 3/1998 | Rosenman | |
| 5,735,853 A | 4/1998 | Olerud | |
| 5,741,282 A | 4/1998 | Anspach, III et al. | |
| 5,743,914 A | 4/1998 | Skiba | |
| 5,772,662 A | 6/1998 | Chapman et al. | |
| 5,782,865 A | 7/1998 | Grptz | |
| 5,810,821 A | 9/1998 | Vandewalle | |
| 5,849,004 A | 12/1998 | Bramlet | |
| 5,871,485 A | 2/1999 | Rao et al. | |
| 5,893,850 A | 4/1999 | Cachia | |
| 5,904,696 A | 5/1999 | Rosenman | |
| 5,908,422 A | 6/1999 | Bresina | |
| 5,928,235 A | 7/1999 | Friedl | |
| 5,928,244 A | 7/1999 | Tovey et al. | |
| 5,931,870 A | 8/1999 | Cuckler et al. | |
| 5,935,129 A | 8/1999 | McDevitt et al. | |
| 5,947,999 A | 9/1999 | Groiso | |
| 5,948,000 A | 9/1999 | Larsen et al. | |
| 5,954,722 A | 9/1999 | Bono | |
| 5,954,747 A | 9/1999 | Clark | |
| 5,957,924 A | 9/1999 | Tormala et al. | |
| 5,968,044 A | 10/1999 | Nicholson et al. | |
| 5,976,139 A | 11/1999 | Bramlet | |
| 5,984,927 A | 11/1999 | Wenstrom, Jr. et al. | |
| 5,984,966 A | 11/1999 | Kiena et al. | |
| 5,989,255 A | 11/1999 | Pepper et al. | |
| 5,993,459 A | 11/1999 | Larsen et al. | |
| 5,997,538 A | 12/1999 | Asnis et al. | |
| 5,997,541 A | 12/1999 | Schenk | |
| 6,001,100 A | 12/1999 | Sherman et al. | |
| 6,001,101 A | 12/1999 | Augagneur et al. | |
| 6,004,327 A | 12/1999 | Asnis et al. | |
| 6,005,161 A | 12/1999 | Brekke et al. | |
| 6,007,566 A | 12/1999 | Wenstrom, Jr. | |
| 6,007,580 A | 12/1999 | Lehto et al. | |
| 6,010,513 A | 1/2000 | Tormala et al. | |
| 6,015,410 A | 1/2000 | Tormala et al. | |
| 6,019,762 A | 2/2000 | Cole | |
| 6,022,352 A | 2/2000 | Vandewalle | |
| 6,030,162 A | 2/2000 | Huebner | |
| 6,036,701 A | 3/2000 | Rosenman | |
| 6,048,342 A | 4/2000 | Zucherman et al. | |
| 6,066,142 A | 5/2000 | Serbousek et al. | |
| 6,068,648 A | 5/2000 | Cole et al. | |
| 6,083,244 A | 7/2000 | Lubbers et al. | |
| 6,102,914 A | 8/2000 | Bulstra et al. | |

(56) References Cited

U.S. PATENT DOCUMENTS

| | | |
|---|---|---|
| 6,123,711 A | 9/2000 | Winters |
| 6,126,661 A | 10/2000 | Faccioli et al. |
| 6,126,663 A | 10/2000 | Hair |
| 6,146,384 A | 11/2000 | Lee et al. |
| 6,161,350 A | 12/2000 | Espinosa |
| 6,162,234 A | 12/2000 | Freedland et al. |
| 6,168,595 B1 | 1/2001 | Durham et al. |
| 6,183,472 B1 | 2/2001 | Lutz |
| 6,183,474 B1 | 2/2001 | Bramlet et al. |
| 6,248,108 B1 | 6/2001 | Tormala et al. |
| 6,251,111 B1 | 6/2001 | Barker et al. |
| 6,267,765 B1 | 7/2001 | Taylor et al. |
| 6,267,767 B1 | 7/2001 | Strobel et al. |
| 6,287,313 B1 | 9/2001 | Sasso |
| 6,290,701 B1 | 9/2001 | Enayati |
| 6,306,136 B1 | 10/2001 | Baccelli |
| 6,319,254 B1 | 11/2001 | Giet et al. |
| 6,348,053 B1 | 2/2002 | Cachia |
| 6,355,043 B1 | 3/2002 | Adam |
| 6,361,537 B1 | 3/2002 | Anderson |
| 6,361,538 B1 | 3/2002 | Fenaroli et al. |
| 6,371,989 B1 | 4/2002 | Chauvin et al. |
| 6,379,355 B1 | 4/2002 | Zucherman et al. |
| 6,379,363 B1 | 4/2002 | Herrington et al. |
| 6,423,061 B1 | 7/2002 | Bryant |
| 6,423,067 B1 | 7/2002 | Eisermann |
| 6,440,169 B1 | 8/2002 | Elberg et al. |
| 6,458,134 B1 | 10/2002 | Songer et al. |
| 6,468,277 B1 | 10/2002 | Justin et al. |
| 6,468,309 B1 | 10/2002 | Lieberman |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,491,714 B1 | 12/2002 | Bennett |
| 6,506,192 B1 | 1/2003 | Gertzman et al. |
| 6,511,481 B2 | 1/2003 | von Hoffmann et al. |
| 6,517,543 B1 | 2/2003 | Berrevoets et al. |
| 6,520,907 B1 | 2/2003 | Foley et al. |
| 6,527,774 B2 | 3/2003 | Lieberman |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,554,831 B1 | 4/2003 | Rivard et al. |
| 6,558,389 B2 | 5/2003 | Clark et al. |
| 6,562,046 B2 | 5/2003 | Sasso |
| 6,579,293 B1 | 6/2003 | Chandran |
| 6,582,453 B1 | 6/2003 | Tran et al. |
| 6,585,730 B1 | 7/2003 | Foerster |
| 6,585,740 B2 | 7/2003 | Schlapfer et al. |
| 6,589,249 B2 | 7/2003 | Sater et al. |
| 6,599,297 B1 | 7/2003 | Carlsson et al. |
| 6,610,091 B1 | 8/2003 | Reiley |
| 6,613,050 B1 | 9/2003 | Wagner et al. |
| 6,626,944 B1 | 9/2003 | Taylor |
| 6,632,224 B2 | 10/2003 | Cachia et al. |
| 6,635,059 B2 | 10/2003 | Randall et al. |
| 6,648,890 B2 | 11/2003 | Culbert et al. |
| 6,648,893 B2 | 11/2003 | Dudasik |
| 6,669,698 B1 | 12/2003 | Tromanhauser et al. |
| 6,669,729 B2 | 12/2003 | Chin |
| 6,673,074 B2 | 1/2004 | Shluzas |
| 6,685,706 B2 | 2/2004 | Padget et al. |
| 6,692,499 B2 | 2/2004 | Tormalaet et al. |
| 6,733,534 B2 | 5/2004 | Sherman |
| 6,752,831 B2 | 6/2004 | Sybert et al. |
| 6,761,720 B1 | 7/2004 | Senegas |
| 6,770,075 B2 | 8/2004 | Howland |
| 6,796,983 B1 | 9/2004 | Zucherman et al. |
| 6,808,526 B1 | 10/2004 | Magerl et al. |
| 6,835,205 B2 | 12/2004 | Atkinson et al. |
| 6,875,215 B2 | 4/2005 | Taras et al. |
| 6,887,243 B2 | 5/2005 | Culbert et al. |
| 6,890,333 B2 | 5/2005 | von Hoffmann et al. |
| 6,908,465 B2 | 6/2005 | von Hoffmann et al. |
| 6,916,323 B2 | 7/2005 | Kitchens et al. |
| 6,921,403 B2 | 7/2005 | Cragg et al. |
| 6,929,606 B2 | 8/2005 | Ritland |
| 6,942,668 B2 | 9/2005 | Padget et al. |
| 6,945,975 B2 | 9/2005 | Dalton |
| 6,949,100 B1 | 9/2005 | Venturini |
| 6,951,561 B2 | 10/2005 | Warren et al. |
| 7,060,068 B2 | 6/2006 | Tromanhauser et al. |
| 7,063,701 B2 | 6/2006 | Michelson |
| 7,063,702 B2 | 6/2006 | Michelson |
| 7,070,601 B2 | 7/2006 | Culbert et al. |
| 7,074,203 B1 | 7/2006 | Johanson et al. |
| 7,094,239 B1 | 8/2006 | Michelson |
| 7,326,211 B2 | 2/2008 | Padget et al. |
| 7,556,629 B2 | 7/2009 | von Hoffmann et al. |
| 2001/0027320 A1 | 10/2001 | Sasso |
| 2001/0049529 A1 | 12/2001 | Cachia et al. |
| 2001/0049530 A1 | 12/2001 | Culbert et al. |
| 2002/0055740 A1 | 5/2002 | Lieberman |
| 2002/0143331 A1 | 10/2002 | Zucherman et al. |
| 2002/0143334 A1 | 10/2002 | Von Hoffmann et al. |
| 2002/0143335 A1 | 10/2002 | Von Hoffmann et al. |
| 2003/0028250 A1 | 2/2003 | Reiley et al. |
| 2003/0065330 A1 | 4/2003 | Zucherman et al. |
| 2003/0069582 A1 | 4/2003 | Culbert |
| 2003/0220643 A1 | 11/2003 | Ferree |
| 2003/0229350 A1 | 12/2003 | Kay |
| 2004/0006391 A1 | 1/2004 | Reiley |
| 2004/0049190 A1 | 3/2004 | Biedermann et al. |
| 2004/0097941 A1 | 5/2004 | Weiner et al. |
| 2004/0127906 A1 | 7/2004 | Culbert et al. |
| 2004/0143734 A1 | 7/2004 | Buer et al. |
| 2004/0199162 A1 | 10/2004 | Von Hoffmann et al. |
| 2004/0225292 A1 | 11/2004 | Sasso et al. |
| 2004/0254575 A1 | 12/2004 | Obenchain et al. |
| 2004/0260297 A1 | 12/2004 | Padget et al. |
| 2005/0033434 A1 | 2/2005 | Berry |
| 2005/0090833 A1 | 4/2005 | Di Poto |
| 2005/0119657 A1 | 6/2005 | Goldsmith |
| 2005/0131411 A1 | 6/2005 | Culbert |
| 2005/0137595 A1 | 6/2005 | von Hoffmann et al. |
| 2005/0143734 A1 | 6/2005 | Cachia et al. |
| 2005/0149030 A1 | 7/2005 | Serhan |
| 2005/0177240 A1 | 8/2005 | Blain |
| 2005/0216026 A1 | 9/2005 | Culbert |
| 2005/0251142 A1 | 11/2005 | von Hoffmann et al. |
| 2005/0283238 A1 | 12/2005 | Reiley |
| 2006/0015105 A1 | 1/2006 | Warren et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0058790 A1 | 3/2006 | Carl et al. |
| 2006/0079908 A1 | 4/2006 | Lieberman |
| 2006/0084977 A1 | 4/2006 | Lieberman |
| 2006/0085010 A1 | 4/2006 | Lieberman |
| 2006/0100707 A1 | 5/2006 | Stinson et al. |
| 2006/0122609 A1 | 6/2006 | Mirkovic et al. |
| 2006/0122610 A1 | 6/2006 | Culbert et al. |
| 2006/0195103 A1 | 8/2006 | Padget et al. |
| 2006/0217711 A1 | 9/2006 | Stevens et al. |
| 2007/0016191 A1 | 1/2007 | Culbert et al. |
| 2007/0118132 A1 | 5/2007 | Culbert et al. |
| 2007/0123868 A1 | 5/2007 | Culbert et al. |
| 2008/0097436 A1 | 4/2008 | Culbert et al. |
| 2008/0108996 A1 | 5/2008 | Padget et al. |
| 2008/0306537 A1 | 12/2008 | Culbert |
| 2009/0069813 A1 | 3/2009 | von Hoffmann et al. |
| 2014/0142629 A1 | 5/2014 | von Hoffmann et al. |

FOREIGN PATENT DOCUMENTS

| | | |
|---|---|---|
| DE | 201 01 793 U1 | 5/2001 |
| EP | 0 525 352 A1 | 2/1993 |
| EP | 0 625 336 | 11/1994 |
| EP | 1 046 376 A1 | 4/2000 |

(56) References Cited

FOREIGN PATENT DOCUMENTS

| | | |
|---|---|---|
| EP | 0 853 929 B1 | 9/2002 |
| EP | 1 378 205 A1 | 7/2003 |
| EP | 1 757 529 A1 | 2/2007 |
| EP | 2 100 565 | 9/2009 |
| EP | 1 523 278 | 11/2009 |
| FR | 2 699 065 | 12/1992 |
| FR | 2 728 778 | 12/1994 |
| FR | 2 745 709 | 3/1996 |
| FR | 2 800 601 | 11/1999 |
| FR | 2 801 189 | 11/1999 |
| FR | 2 808 182 | 4/2000 |
| GB | 2157788 A | 10/1985 |
| GB | 2173565 A | 10/1986 |
| JP | 64-52439 | 2/1989 |
| JP | 6-319742 A | 11/1994 |
| JP | 10-085232 A | 4/1998 |
| JP | 11-089854 A | 4/1999 |
| JP | 2005-533627 | 11/2005 |
| WO | WO 91/09572 | 12/1989 |
| WO | WO 99/62417 | 12/1999 |
| WO | WO 00/67652 | 5/2000 |
| WO | WO 01/80751 | 11/2001 |
| WO | WO 02/43601 | 6/2002 |
| WO | WO 03/043488 | 5/2003 |
| WO | WO 2004/008949 | 1/2004 |
| WO | WO 2004/0008949 | 1/2004 |
| WO | WO 2004/064603 | 8/2004 |
| WO | WO 2004/078220 | 9/2004 |
| WO | WO 2004/078221 | 9/2004 |
| WO | WO 2004/098453 | 11/2004 |
| WO | WO 2006/063083 | 6/2006 |
| WO | WO 2007/124130 | 4/2008 |

\* cited by examiner

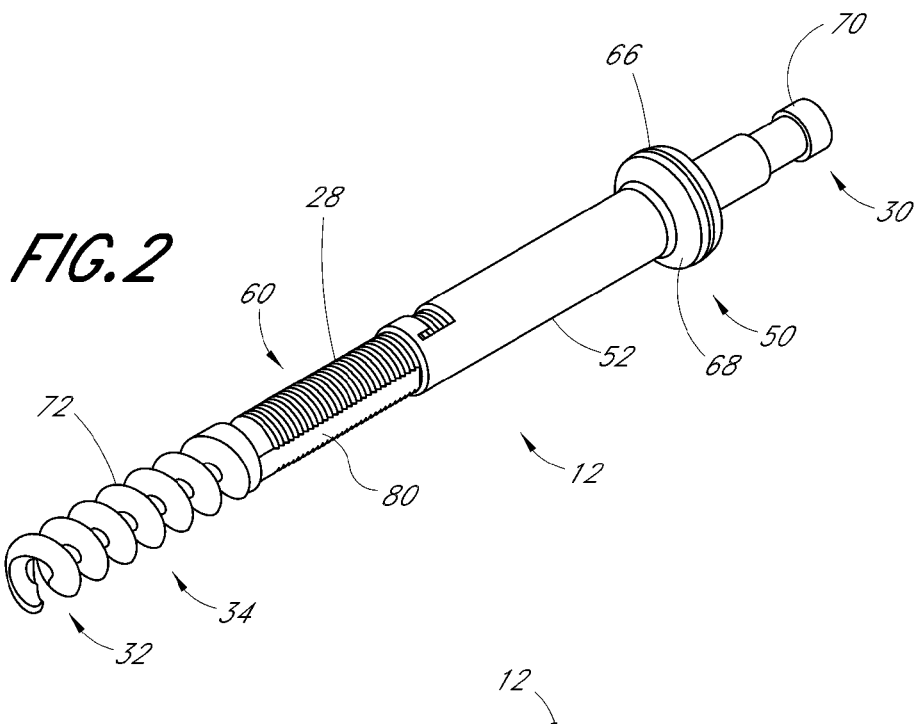
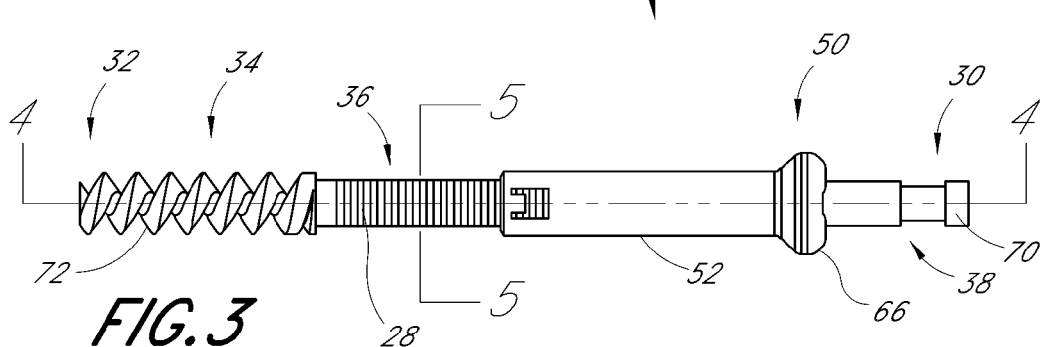
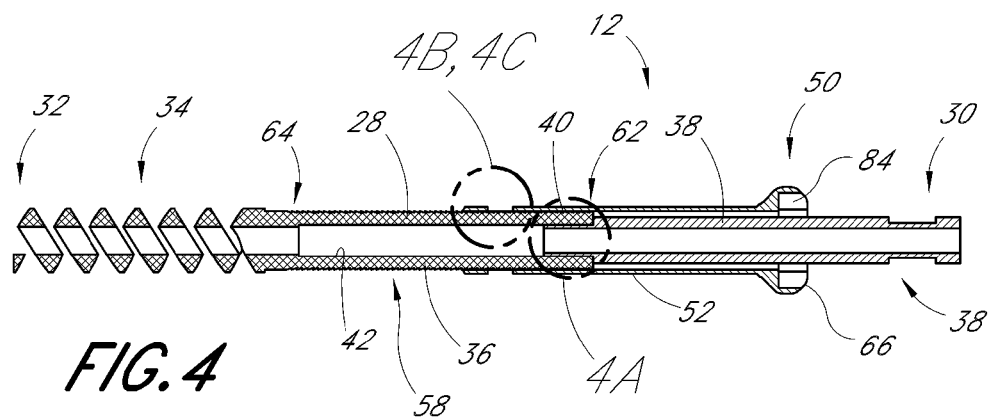

METHOD AND APPARATUS FOR BONE FIXATION WITH SECONDARY COMPRESSION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

1. Field of the Invention

The present invention relates to internal bone fracture and fusion fixation devices. In one application, the present invention relates to bone fracture fixation devices and methods adapted for fixation, among other fractures, of femoral neck and other proximal femoral fractures.

2. Description of the Related Art

The femur, otherwise known as the thigh bone, generally comprises an elongated shaft extending from the hip to the knee. The proximal end of the shaft includes a head, a neck, a greater trochanter and a lesser trochanter. The head of the femur fits into the acetabular cup of the hip bone to form a ball and socket joint at the hip. The distal end of the femur includes a medial condyle and a lateral condyle. The condyles engage an upper end of the tibia to form the knee joint. Overall, the femur is the longest and strongest bone in the skeleton. However, portions of the femur are extremely susceptible to fracturing.

Pertrochanteric fractures among geriatric patients are the most frequent in connection with those of the region of the neck of the bone. The advanced age and the pathologies which are encountered in these patients make a timely stabilization of skeletal injuries necessary in order to reduce to a minimum the bed confinement and the rehabilitation times. Preferably, devices and procedures are utilized which minimize complications brought about by the so-called immobilization syndrome, which may be lethal for patients in delicate metabolical circumstances. It is also preferable to reduce to a minimum blood losses related to surgical intervention. At the same time, the syntheses means utilized must be stable in order to allow the patient to very timely assume a seated position and, two or three days following the intervention, to reassume an erect posture with progressive bearing of weight.

Internal fixation of femoral fractures in general is one of the most common orthopedic surgical procedures. Fractures of the femur occur in both the proximal portion of the femur and the distal portion of the femur. Fractures of the proximal portion of the femur (hip fractures) are generally classified as femoral neck fractures, intertrochanteric fractures and subtrochanteric fractures. Fractures of the distal portion of the femur (knee fractures) are referred to as supracondylar fractures. Supracondylar fractures generally extend vertically between the condyles at the lower end of the femur to separate the distal portion of the femur into two main bone fragments. A fracture line may be further comminuted to create a plurality of smaller bone fragments. Fractures of the femur which extend into the neck of the bone are generally more difficult to treat than fractures restricted to the shaft of the femur.

Operative treatment of the fractures requires that the fractures be internally fixed and possibly compressed. Fractures of the neck, head or trochanters of the femur have been treated with a variety of compression screw assemblies which include generally a compression plate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted.

A variety of elongated implants (nail, screw, pin, etc.) have been developed, which are adapted to be positioned along the longitudinal axis of the femoral neck with a leading (distal) end portion in the femoral head so as to stabilize a fracture of the femoral neck. The elongated implant may be implanted by itself or connected to another implant such as a side plate or intramedullary rod. The leading end portion of the implant typically includes means to positively grip the femoral head bone (external threads, expanding arms, etc.), but the inclusion of such gripping means can introduce several significant problems. First, implants with sharp edges on the leading end portion, such as the externally threaded implants, exhibit a tendency to migrate proximally towards the hip joint weight bearing surface after implantation. This can occur when the proximal cortical bone has insufficient integrity to resist distal movement of the screw head. Such proximal migration under physiological loading, which is also referred to as femoral head cut-out, can lead to significant damage to the adjacent hip joint. Also, the externally threaded implants can generate large stress concentrations in the bone during implantation which can lead to stripping of the threads formed in the bone and thus a weakened grip. The movable arms of known expanding arm devices are usually free at one end and attached at the other end to the main body of the leading end portion of the implant. As a result, all fatigue loading is concentrated at the attached ends of the arms and undesirably large bending moments are realized at the points of attachment. In addition, conventional threaded implants generally exhibit insufficient holding power under tension, such that the threads can be stripped out of the femoral head either by overtightening during the implantation procedure or during post operative loading by the patient's weight.

Thus, notwithstanding the variety of efforts in the prior art, there remains a need for an orthopedic fixation device with improved locking force such as within the femoral head in a femoral neck application, which resists migration and rotation, and which can be easily and rapidly deployed within the bone.

SUMMARY

There is provided in accordance with one aspect of the present invention, a method of securing a first bone fragment to a second bone fragment. The method comprises the steps of drilling a bore through the first bone fragment in the direction of the second bone fragment, and advancing through the bore a fixation device comprising a first portion and a second portion that are coupled to each other. A distal anchor of the fixation device is rotated to secure the fixation device to the second fragment, and the proximal anchor is axially advanced to engage the first fragment.

In one application of the method, the second bone fragment comprises the head of a femur. Alternatively, the second bone fragment comprises a tibia, a fibula, a femur, a humurus, a radius, or an ulna. The first bone fragment may comprise a condyle.

The method may additionally comprise the step of uncoupling the first portion from the second portion.

In accordance with another aspect of the present invention, there is provided a femoral neck fracture fixation device. The device comprises an elongated body, having a proximal end and a distal end. A helical distal anchor is provided on the distal end. In some embodiments, the distal anchor includes a cutting tip. A first retention structure is provided on the body, proximal to the distal anchor, and a proximal anchor surface is moveably carried by the body. The proximal anchor includes a tubular sleeve that in some embodiments includes a plurality of graduations positioned on an outer surface of the tubular sleeve. The proximal anchor surface is moveable in the distal direction with respect to the body. The retention structure resists proximal movement of the proximal anchor surface with respect to the body.

In one embodiment, the first retention structure comprises a series of ridges or grooves. A second retention structure is preferably provided on the interior of the tubular sleeve for cooperating with the first retention structure on the body.

In accordance with another aspect of the present invention, there is provided a method of treating a femoral fracture. The method comprises the steps of drilling at least one and preferably two or three bores distally into the femur in the direction of a fracture, and advancing into each bore a fixation device that comprises a body having a first portion that forms a distal bone anchor and a second portion that forms a proximal end. A proximal component is rotated to engage the distal anchor with the bone distal to the fracture, and a proximal anchor is advanced distally along the fixation device to compress the fracture.

Preferably, the drilling step comprises drilling the bore along an axis which extends through the femoral neck and in the direction of the head of the femur. In one embodiment, the advancing a proximal anchor step comprises axially advancing the proximal anchor without rotating the proximal anchor with respect to the fixation device. The femoral fracture may be a capital fracture, subcapital fracture, femoral neck fracture, an intertrochanteric fracture or a subtrochanteric fracture.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 2 is a side perspective view of a fixation device similar to that of FIG. 1.

FIG. 3 is a side elevational view of the fixation device of FIG. 2.

FIG. 4 is a cross-sectional view taken through line 4-4 of FIG. 3.

DETAILED DESCRIPTION

Figure 1:
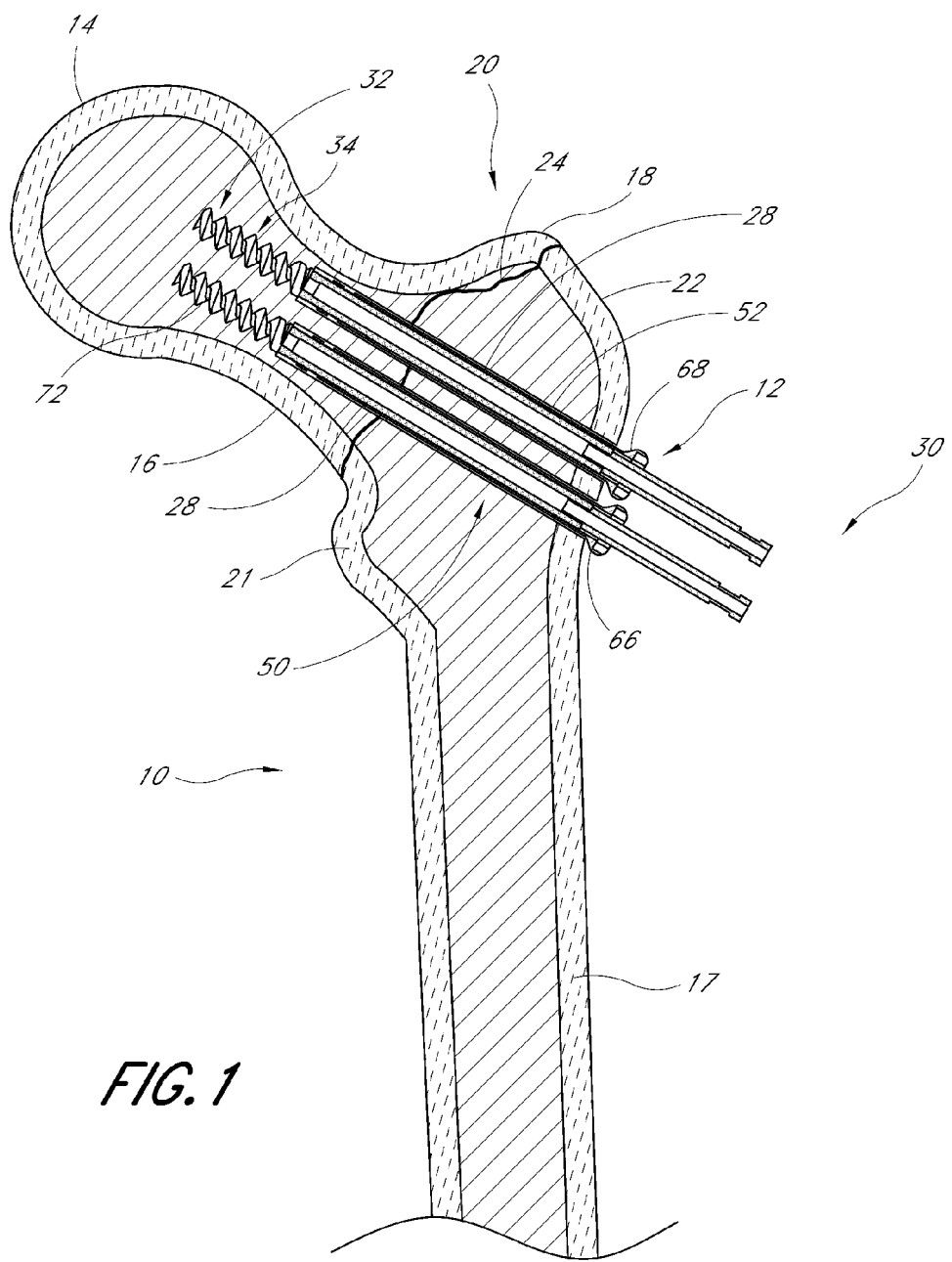
FIG. 1 is a posterior elevational posterior cross section through the proximal portion of the femur, illustrating two femoral neck fracture fixation devices positioned therein.

Although the fixation devices of the present invention will be disclosed primarily in the context of fractures of the proximal femur, the methods and structures disclosed herein are intended for application in any of a wide variety of bones and fractures, as will be apparent to those of skill in the art in view of the disclosure herein. For example, the bone fixation device of the present invention is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present invention. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. The bone fixation device may be used with or without plate(s) or washer (s), all of which can be either permanent, absorbable, or combinations.

Fractures of the fibular and tibial malleoli, pilon fractures and other fractures of the bones of the leg may be fixated and stabilized with the present invention with or without the use of plates, both absorbable or non-absorbing types, and with alternate embodiments of the current invention. The device may also be used for also be used for ankle fusions, fixating and stabilizing fractures and osteotomies of the mid and hind foot, Lisfranc fractures, triple arthrodesis, tarsal arthrodesis and osteotomy, or others as are known to those with skill in the art. One example is the fixation of the medial malleolar avulsion fragment.

The fixation device of the present invention may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The fixation device may also be used to attach sutures to the bone, such as in any of a variety of tissue suspension procedures.

For example, peripheral applications for the fixation devices include utilization of the device for fastening soft tissue such as capsule, tendon or ligament to bone. It may also be used to attach a synthetic material such as marlex mesh, to bone or allograft material such as tensor fascia lata, to bone. In the process of doing so, retention of the material to bone may be accomplished with the collar as shown, or the pin and or collar may be modified to accept a suture or other material for facilitation of this attachment.

Specific examples include attachment of the posterior tibial tendon to the navicular bone in the Kidner operation. This application may be accomplished using an appropriately sized implant of the present invention along with a washer with distally extending soft tissue spikes. Navicular-cuneiform arthrodesis may be performed utilizing the device and concurrent attachment of the tendon may be accomplished. Attachment of the tendon may be accomplished in the absence of arthrodesis by altering the placement of the implant in the adjacent bone.

Ligament or capsule reattachment after rupture, avulsion or detachment, such as in the ankle, shoulder or knee can also be accomplished using the devices disclosed herein.

The fixation devices may be used in combination with semi tubular, one-third tubular and dynamic compression plates, both of metallic and absorbable composition, if the collar is modified to match the opening on the plate.

The cannulated design disclosed below can be fashioned to accept an antibiotic impregnated rod for the slow adsorption of medication locally. This may be beneficial for prophylaxis, especially in open wounds, or when osteomyelitis is present and stabilization of fracture fragments is indicated.

A kit may be assembled for field use by military or sport medical or paramedical personnel. This kit contains an implanting tool, and a variety of implant device size and types. The kit may include additional components such as sterilization or disinfectant materials, a skin stapler, bandages, gloves, and basic tools for emergent wound and fracture treatment. Antibiotic rods may be included for wound prophylaxis during transport.

Referring to FIG. 1, there is illustrated a posterior side elevational view of the proximal portion of a femur 10, having a fixation device 12 positioned therein. The proximal end of the femur 10 comprises a head 14 connected by way of a neck 16 to the long body or shaft 17 of the femur 10. As illustrated in FIG. 1, the neck 16 is smaller in diameter than the head 14. The neck 16 and head 14 also lie on an axis which, on average in humans, crosses the longitudinal axis of the body 17 of the femur 10 at an angle of about 126.degree. The risk of fracture at the neck 16 is thus elevated, among other things, by the angular departure of the neck 16 from the longitudinal axis of the body 17 of femur 10 and also the reduced diameter of the neck 16 with respect to the head 14.

The greater trochanter 18 extends outwardly above the junction of the neck 16 and the body 17 of the femur 10. On the medial side of the greater trochanter 18 is the trochanteric fossa 20. This depression accommodates the insertion of the obturator externus muscle. The lesser trochanter 21 is located posteromedially at the junction of the neck 16 and the body 17 of the femur 10. Both the greater trochanter 18 and the lesser trochanter 21 serve for the attachment of muscles. On the posterior surface of the femur 10 at about the same axial level as the lesser trochanter 21 is the gluteal tuberosity 22, for the insertion of the gluteus maximus muscle. Additional details of the femur are well understood in the art and not discussed in further detail herein.

FIG. 1 illustrates a fracture 24 which crosses the femur approximately in the area of the greater trochanter 18. Fractures of the proximal portion of the femur 10 are generally classified as capital or subcapital fractures, femoral neck fractures, intertrochanteric fractures and subtrochanteric fractures. All of these fractures will be deemed femoral neck fractures for the purpose of describing the present invention.

Referring to FIGS. 1-4, the fixation device 12 comprises a body 28 extending between a proximal end 30 and a distal end 32. The length, diameter and construction materials of the body 28 can be varied, depending upon the intended clinical application. In embodiments optimized for various fractures in an adult human population, the body 28 will generally be within the range of from about 10 mm to about 150 mm in length after sizing, and within the range of from about 2 mm to about 8 mm in maximum diameter. The major diameter of the helical anchor, discussed below, may be within the range of from about 2.7 mm to about 12 mm. In general, the appropriate dimensions of the body 28 will vary, depending upon the specific fracture. In rough terms, for a malleolar fracture, shaft diameters in the range of from about 3 mm to about 4.5 mm may be used, and lengths within the range of from about 25 mm to about 70 mm. For condylar fractures, shaft diameters within the range of from about 3.5 mm to about 6.5 mm may be used with lengths within the range of from about 25 mm to about 70 mm. For colles fractures (distal radius and ulna), diameters within the range of from about 2.0 mm to about 4.5 mm may be used with any of a variety of lengths within the range of from about 6 mm to about 70 mm.

In one embodiment, the body 28 comprises titanium. However, as will be described in more detail below, other metals or bioabsorbable or nonabsorbable polymeric materials may be utilized, depending upon the dimensions and desired structural integrity of the finished fixation device 12.

The distal end 32 of the body 28 is provided with a cancellous bone anchor or distal cortical bone anchor 34. Additional details of the distal bone anchor are described below. In general, in a femoral neck application, distal bone anchor 34 is adapted to be rotationally inserted into the cancellous bone within the head 14 of the femur 10, to retain the fixation device 12 within the femoral head.

Figure 4A:
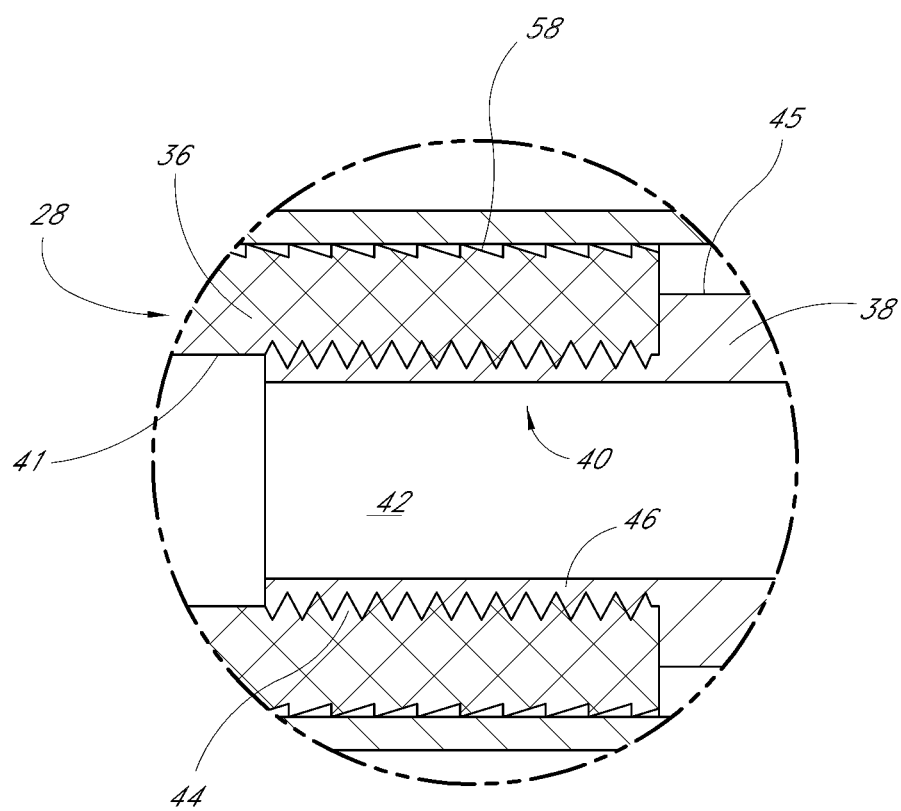
FIG. 4A is an enlarged view of portion 4A of FIG. 4.

Referring to FIGS. 3, 4, and 4A, the body 28 comprises a first portion 36 and a second portion 38 that are coupled together at a junction 40. In the illustrated embodiment, the first portion 36 carries the distal anchor 34 while the second portion 38 forms the proximal end 30 of the body 28. The first and second portions 36, 38 are preferably detachably coupled to each other at the junction 40. In the illustrated embodiment, the first and second portions 36, 38 are detachably coupled to each other via interlocking threads. Specifically, as best seen in FIG. 4A, the body 28 includes an inner surface 41, which defines a central lumen 42 that preferably extends from the proximal end 30 to the distal end 32 throughout the body 28. At the proximal end of the first portion 36, the inner surface 41 includes a first threaded portion 44. The first threaded portion 44 is configured to mate with a second threaded portion 46, which is located on the outer surface 45 of the second portion 38. The interlocking annular threads of the first and second threaded portions 44, 46 allow the first and second portions 36, 38 to be detachably coupled to each other. In one modified embodiment, the orientation of the first and second threaded portions 44, 46 can be reversed. That is, the first threaded portion 44 can be located on the outer surface of the first portion 36 and the second threaded portion 46 can be located on the inner surface 41 at the distal end of the second portion 38. Any of a variety of other releasable complementary engagement structures may also be used, to allow removal of second portion 38 following implantation, as is discussed below.

In a modified arrangement, the second portion 38 can comprise any of a variety of tensioning elements for permitting proximal tension to be placed on the distal anchor 34 while the proximal anchor is advanced distally to compress the fracture. For example, any of a variety of tubes or wires can be removably attached to the first portion 36 and extend proximally to the proximal handpiece. In one such arrangement, the first portion 36 can include a releasable connector in the form of a latching element, such as an eye or hook. The second portion 38 can include a complementary releasable connector (e.g., a complementary hook) for engaging the first portion 36. In this manner, the second portion 38 can be detachably coupled to the first portion 36 such proximal traction can be applied to the first portion 36 through the second portion as will be explained below. Alternatively, the second portion 48 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein.

The proximal end 30 of the fixation device is provided with a proximal anchor 50. Proximal anchor 50 is axially distally moveable along the body 28, to permit compression of the fracture 24 as will be apparent from FIG. 1 and the description below. As will be explained below, complimentary locking structures such as threads or ratchet like structures between the proximal anchor 50 and the body 28 resist proximal movement of the anchor 50 with respect to the body 28 under normal use conditions. The proximal anchor 50 preferably can be axially advanced along the body 28 without rotation as will be apparent from the disclosure herein.

Figure 4B:
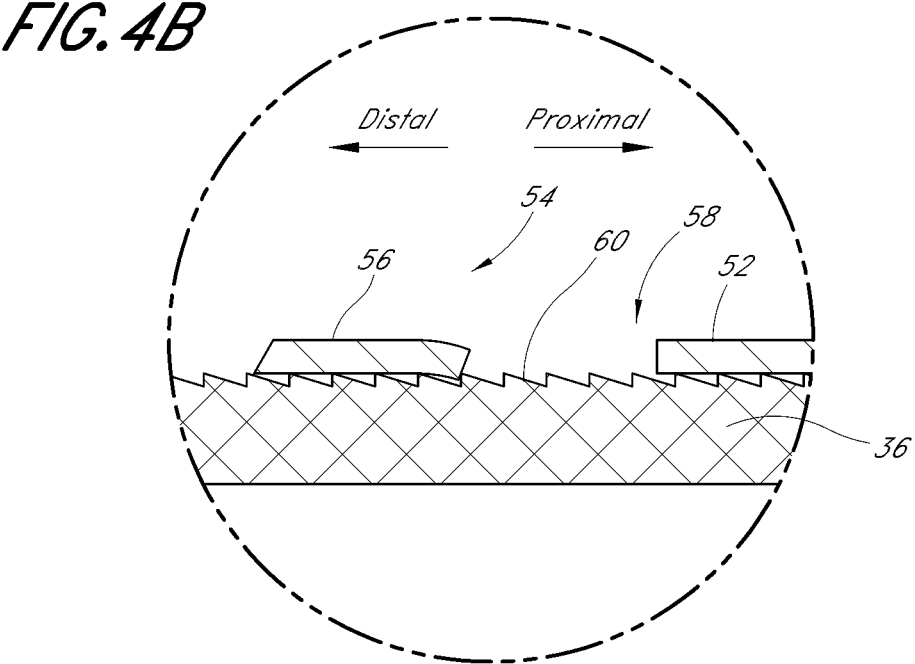
FIG. 4B is an enlarged view of portion 4B of FIG. 4 with the fixation device in a first position.
Figure 4C:
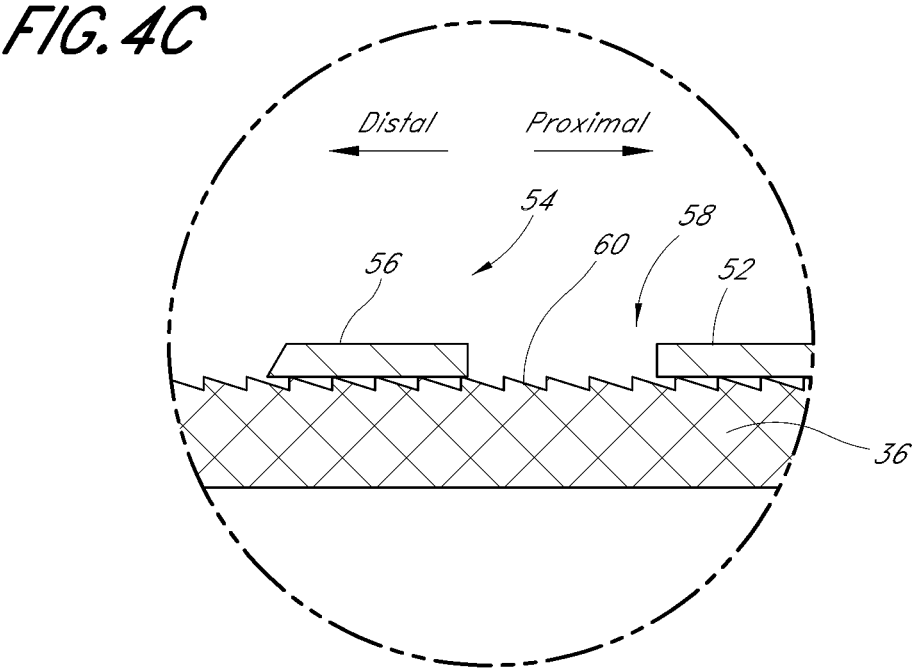
FIG. 4C is an enlarged view of portion 4C of FIG. 4 with the fixation device in a second position.

In the illustrated embodiment, proximal anchor 50 comprises a housing 52 such as a tubular body, for coaxial movement along the body 28. As best seen in FIGS. 1 and 4, in a final position, the housing 52 extends distally past the junction 40 between the first portion 36 and the second portion 38. The housing 52 is provided with one or more surface structures 54 such as a radially inwardly projecting flange 56 (see FIGS. 4B and 4C), for cooperating with complementary surface structures 58 on the first portion 36 of the body 28. In the illustrated embodiment, the complimentary surface structures 58 comprise a series of annular ridges or grooves 60. The surface structures 54 and complementary surface structures 58 permit distal axial travel of the proximal anchor 50 with respect to the body 28, but resist proximal travel of the proximal anchor 50 with respect to the body 28.

For example, as best seen in FIG. 4B, the proximal end of the flange 56 is biased towards the longitudinal axis of the body 28. As such, when the proximal anchor 50 is urged proximally with respect to the body 28, the flange 56 engages the grooves or ridges 60 of the complementary surface structures 58. This prevents proximal movement of the proximal anchor 50 with respect to the body 28. In contrast, as best seen in FIG. 4C, when the proximal anchor 50 is moved distally with respect to the body 28, the flange 56 can bend outwardly away from the body 28 and the ridges 60 so as to allow the proximal anchor 50 to move distally. Of course, those of skill in the art will recognize that there are a variety of other complementary surface structures, which permit one way ratchet like movement. For example, a plurality of annular rings or helical threads, ramped ratchet structures and the like for cooperating with an opposing ramped structure or pawl can also be used. In one embodiment, opposing screw threads are dimensioned to function as a ratchet.

Retention structures 58 are spaced axially apart along the body 28, between a proximal limit 62 and a distal limit 64. The axial distance between proximal limit 62 and distal limit 64 is related to the desired axial working range of the proximal anchor 50, and thus the range of functional sizes of the fixation device 12. Thus, the present invention provides a bone fixation device which can provide compression across a fracture throughout a range of motion following the placement of the distal anchor. The distal anchor may be positioned within the cancellous and/or distal cortical bone, and the proximal anchor may be distally advanced throughout a range to provide compression across the fracture without needing to relocate the distal anchor and without needing to initially locate the distal anchor in a precise position with respect to the proximal side of the bone. Providing a working range throughout which tensioning of the proximal anchor is independent from setting the distal anchor allows a single device to be useful for a wide variety of fractures, as well as eliminates the need for accurate device measurement and accurate placement of the distal anchor. In many applications, the working range is at least about 10% of the overall length of the device, and may be as much as 20% or 30% or more of the overall device length. In the context of a femoral application, working ranges of up to about 10 mm or more may be provided, since estimates within that range can normally be readily accomplished within the clinical setting. In other applications, such as a metatarsal fracture, a working range in the area of from about 1 mm to about 2 mm may be all that is necessary. The embodiments disclosed herein can be scaled to have a greater or a lesser working range, as will be apparent to those of skill in the art in view of the disclosure herein.

The proximal anchor 50 includes a flange 66 that seats against the outer surface of the femur or tissue adjacent the femur. The flange 66 is preferably an annular flange, to optimize the footprint or contact surface area between the flange 66 and the femur. Circular or polygonal shaped flanges for use in femoral head fixation will generally have a diameter of at least about 4 mm greater than the adjacent body 28 and often within the range of from about 4 mm to about 20 mm or more greater than the adjacent body 28.

In the illustrated embodiment, the bone contacting surface 68 of the flange 44 is tapered and generally faces the shaft 17 of the femur 10. In other embodiments, the bone contacting surface 69 can resides in or approximately on a plane, which is perpendicular with respect to the longitudinal axis of the body 28. In other embodiments, other angular relationships between the bone contacting surface 68 of the flange 66 and the longitudinal axis of the body 28 and housing 52 may be utilized, depending upon the anticipated entrance angle of the body 28 and associated entrance point surface of the femur 10. In general, the longitudinal axis extending through the head 14 and neck 16 of the human femur is inclined at an angle of approximately 126.degree. from the longitudinal axis of the long body 17 of the femur 10. Angles between the longitudinal axis of body 28 and tissue contacting surface 68 within the range of from about 90.degree. to about 140.degree. will generally be utilized.

In a modified embodiment, the housing 52 of the proximal anchor 50 can include one or more one or more barbs that extend radially outwardly from the tubular housing 52. Such barbs provide for self tightening after the device has been implanted in the patient as described in a co-pending U.S. patent application Ser. No. 10/012,687 entitled DISTAL BONE ANCHORS FOR BONE FIXATION WITH SECONDARY COMPRESSION" filed Nov. 13, 2001, which is hereby expressly incorporated by reference herein. The barbs may be radially symmetrically distributed about the longitudinal axis of the housing 52. Each barb is provided with a transverse engagement surface, for anchoring the proximal anchor 50 in the bone. The transverse engagement surface may lie on a plane which is transverse to the longitudinal axis of the housing 50 or may be inclined with respect to the longitudinal axis of the tubular 50. In either arrangement, the transverse engagement surface 43 generally faces the bone contacting surface 68 of the flange 44. As such, the transverse engagement surface inhibits proximal movement of the proximal anchor with respect to the bone.

The clinician can be provided an array of proximal anchors 50 of varying angular relationships between the bone contacting surface 68 and the longitudinal axis of the body 28 and housing 52 (e.g., 90.degree., 100.degree., 110.degree., 120.degree., and 130.degree.). A single body 28 can be associated with the array such as in a single sterile package. The clinician upon identifying the entrance angle of the body 28 and the associated entrance point surface orientation of the femur 10 can choose the anchor 50 from the array with the best fit angular relationship, for use with the body 28.

With particular reference to FIG. 3, the proximal end 30 of the body 28 may be provided with a rotational coupling 70, for allowing the second portion 38 of the body 28 to be rotationally coupled to a rotation device. The proximal end 30 of the body 28 may be desirably rotated to accomplish one or two discrete functions. In one application of the invention, the proximal end 30 is rotated to remove the second portion 38 of the body 28 following tensioning of the device across a fracture or to anchor an attachment to the bone. Rotation of the rotational coupling 70 may also be utilized to rotationally drive the distal anchor into the bone. Any of a variety of rotation devices may be utilized, such as electric drills or hand tools, which allow the clinician to manually rotate the proximal end 30 of the body. Thus, the rotational coupling 70 may have any of a variety of cross sectional configurations, such as one or more flats or splines.

In one embodiment, the rotational coupling 70 comprises a proximal projection of the body 28 having an axial recess with a polygonal cross section, such as a hexagonal cross section. The rotational coupling 70 is illustrated as a female component, machined or milled or attached to the proximal end 30 of the body 28. However, the rotational coupling may also be in the form of a male element, such as a hexagonal or other noncircular cross sectioned projection.

As illustrated, the body 28 is cannulated to accommodate installation over a placement wire as is understood in the art. The cross section of the illustrated central cannulation is circular but in other embodiments may be non circular, e.g., hexagonal, to accommodate a corresponding male tool for installation or removal of the second portion 38 of the body 28 as will be explained below. In other embodiments, the body 28 may be partially or wholly solid.

In all of the embodiments illustrated herein, the distal anchor 34 comprises a helical locking structure 72 for engaging cancellous and/or distal cortical bone. In the illustrated embodiment, the locking structure 72 comprises a flange that is wrapped around the axial lumen. The flange extends through at least one and generally from about two to about 50 or more full revolutions depending upon the axial length of the distal anchor and intended application. For most femoral neck fixation devices, the flange will generally complete from about 2 to about 20 revolutions. The helical flange 72 is preferably provided with a pitch and an axial spacing to optimize the retention force within cancellous bone, to optimize compression of the fracture.

The helical flange 72 of the illustrated embodiment has a generally triangular cross-sectional shape (see FIG. 4). However, it should be appreciated that the helical flange 72 can have any of a variety of cross sectional shapes, such as rectangular, oval or other as deemed desirable for a particular application through routine experimentation in view of the disclosure herein. The outer edge of the helical flange 72 defines an outer boundary. The ratio of the diameter of the outer boundary to the diameter of the central lumen can be optimized with respect to the desired retention force within the cancellous bone and giving due consideration to the structural integrity and strength of the distal anchor 34. Another aspect of the distal anchor 34 that can be optimized is the shape of the outer boundary and the central core, which in the illustrated embodiment are generally cylindrical.

The distal end 32 and/or the outer edges of the helical flange 72 may be atraumatic (e.g., blunt or soft). This inhibits the tendency of the fixation device 12 to migrate anatomically proximally towards the hip joint bearing surface after implantation (i.e., femoral head cut-out). Distal migration is also inhibited by the dimensions and presence of the proximal anchor 50, which has a larger footprint than conventional screws.

A variety of other arrangements for the distal anchor 32 can also be used. For example, the various distal anchors described in U.S. patent application Ser. No. 09/822,803, filed Mar. 30, 2001, entitled "METHOD AND APPARATUS FOR FIXATION OF PROXIMAL FEMORAL FRACTURES", and co-pending U.S. patent application Ser. No. 10/012,687 entitled "DISTAL BONE ANCHORS FOR BONE FIXATION WITH SECONDARY COMPRESSION", filed Nov. 13, 2001 can be incorporated into the fixation device 12 described herein. The entire contents these applications are hereby expressly incorporated by reference. In particular, the distal anchor may comprise a single helical thread surrounding a central core, much as in a conventional screw, which has been cannulated to facilitate placement over a wire. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal bone, and whether the distal anchor is intended to engage exclusively cancellous bone or will also engage cortical bone.

Figure 5:
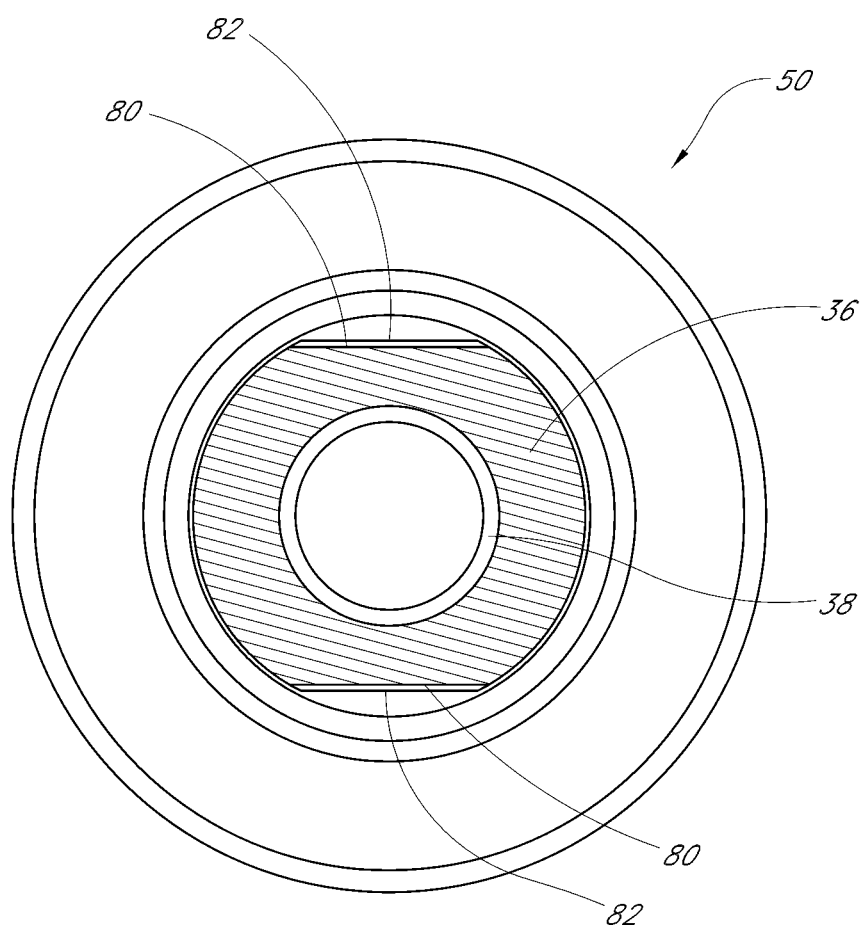
FIG. 5 is a cross-sectional view taken through line 5-5 of FIG. 3.

With particular reference to FIGS. 2 and 5, the fixation device may include an antirotation lock between the first portion 36 of the body 28 and the proximal collar 50. In the illustrated embodiment, the first portion 36 includes a pair of flat sides 80, which interact with corresponding flat structures 82 in the proximal collar 50. One or three or more axially extending flats may also be used. As such, rotation of the proximal collar 50 is transmitted to the first portion 36 and distal anchor 34 of the body 28. Of course, those of skill in the art will recognize various other types of splines or other interfit structures can be used to prevent relative rotation of the proximal anchor and the first portion 36 of the body 28.

To rotate the proximal collar, the flange 66 is preferably provided with a gripping structure to permit an insertion tool to rotate the flange 66. Any of a variety of gripping structures may be provided, such as one or more slots, flats, bores or the like. In one embodiment, the flange 44 is provided with a polygonal, and, in particular, a pentagonal or hexagonal recess 84. See FIG. 4.

Figure 6A:
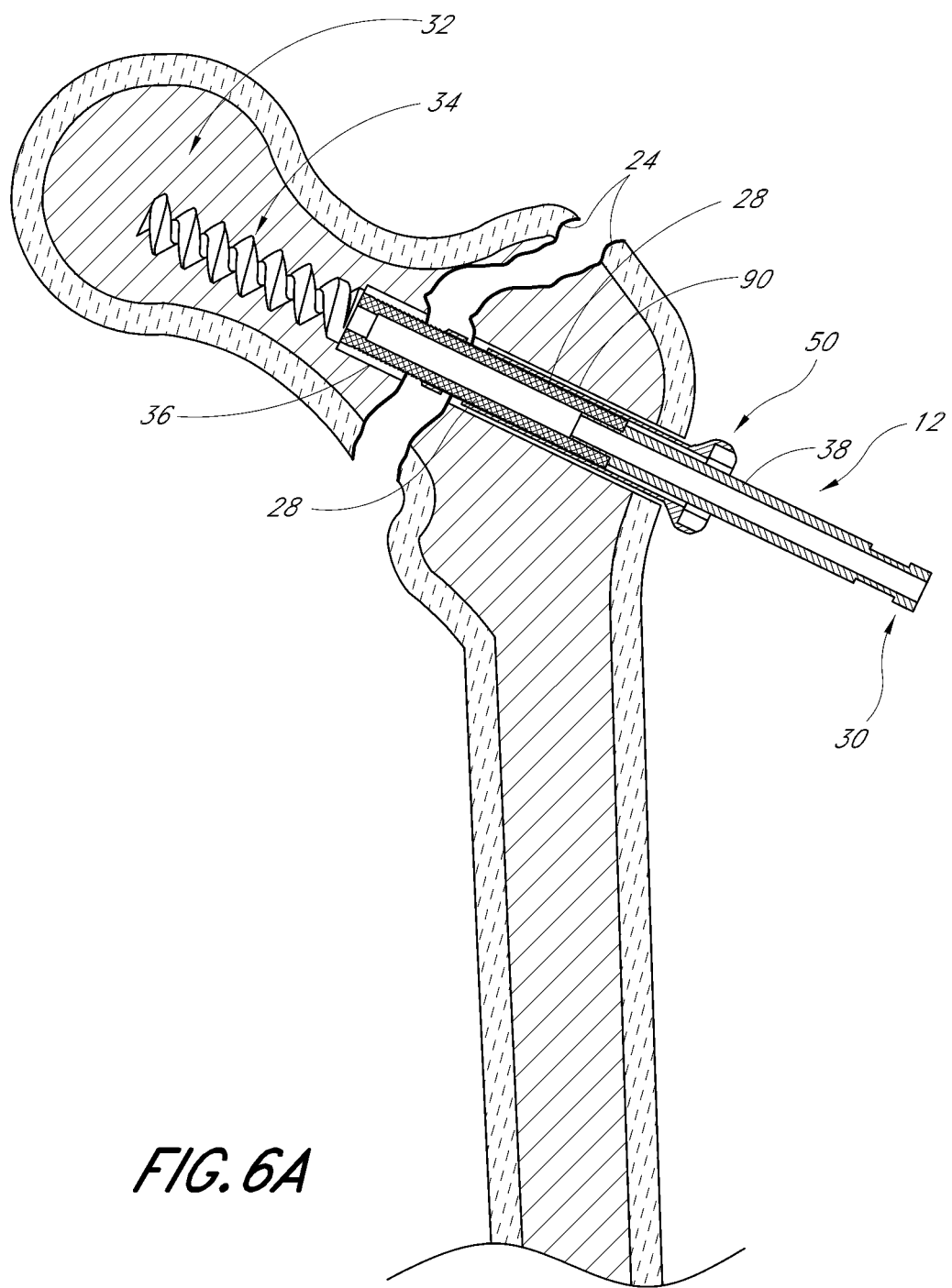
FIGS. 6A-C illustrate a procedure for using of the fixation device of FIG. 1 to secure a femoral neck fracture.

In use, the clinician first identifies a patient having a fracture to be treated, such as a femoral neck fracture, which is fixable by an internal fixation device. The clinician accesses the proximal femur, reduces the fracture if necessary and selects a bone drill and drills a hole 90 (see FIG. 6A) in accordance with conventional techniques. Frequently, the hole 90 has a diameter within the range from about 3 mm to about 8 mm. This diameter may be slightly larger than the diameter of the distal anchor 34. The hole 90 preferably extends up to or slightly beyond the fracture 24.

A fixation device 12 having an axial length and outside diameter suitable for the hole 90 is selected. The distal end 32 of the fixation device 12 is advanced distally into the hole 90 until the distal anchor 34 reaches the distal end of the hole 90. The proximal anchor 50 may be carried by the fixation device 12 prior to advancing the body 28 into the hole 90, or may be attached following placement of the body 28 within the hole 90. Once the body 28 and proximal anchor 50 are in place, the clinician may use any of a variety of driving devices, such as electric drills or hand tools to rotate the proximal anchor 50 and thus cancellous bone anchor 34 into the head of the femur.

Figure 6B:
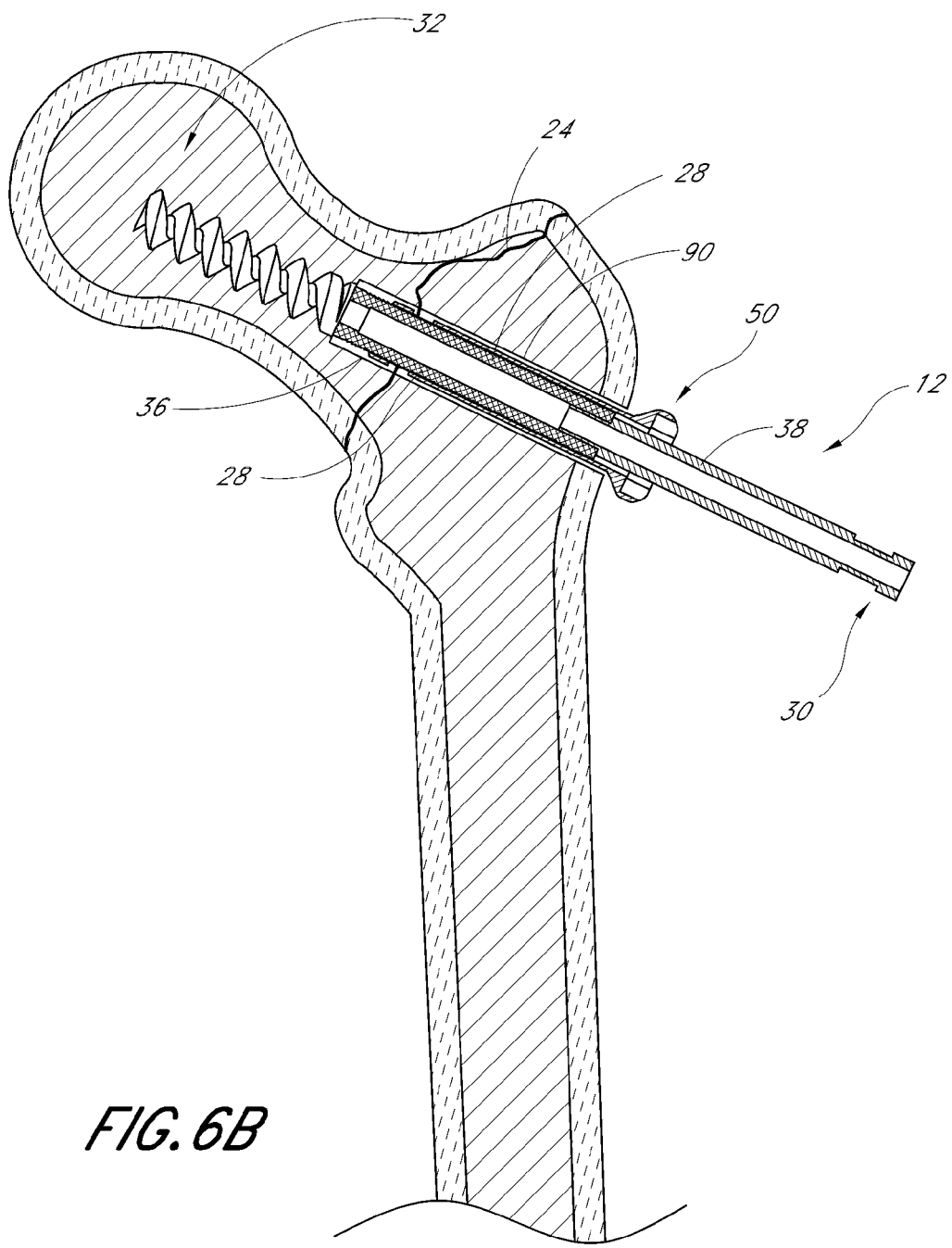

Once the anchor 34 is in the desired location, proximal traction is applied to the proximal end 30 of body 28, such as by conventional hemostats, pliers or a calibrated loading device, while distal force is applied to the proximal anchor 50. In this manner, the proximal anchor 50 is advanced distally until the anchor 50 fits snugly against the outer surface of the femur or tissue adjacent the femur and the fracture 24 is completely reduced as shown in FIG. 6B. Appropriate tensioning of the fixation device 12 is accomplished by tactile feedback or through the use of a calibration device for applying a predetermined load on the implantation device. One advantage of the structure of the present invention is the ability to adjust compression independently of the setting of the distal anchor 34.

Figure 6C:
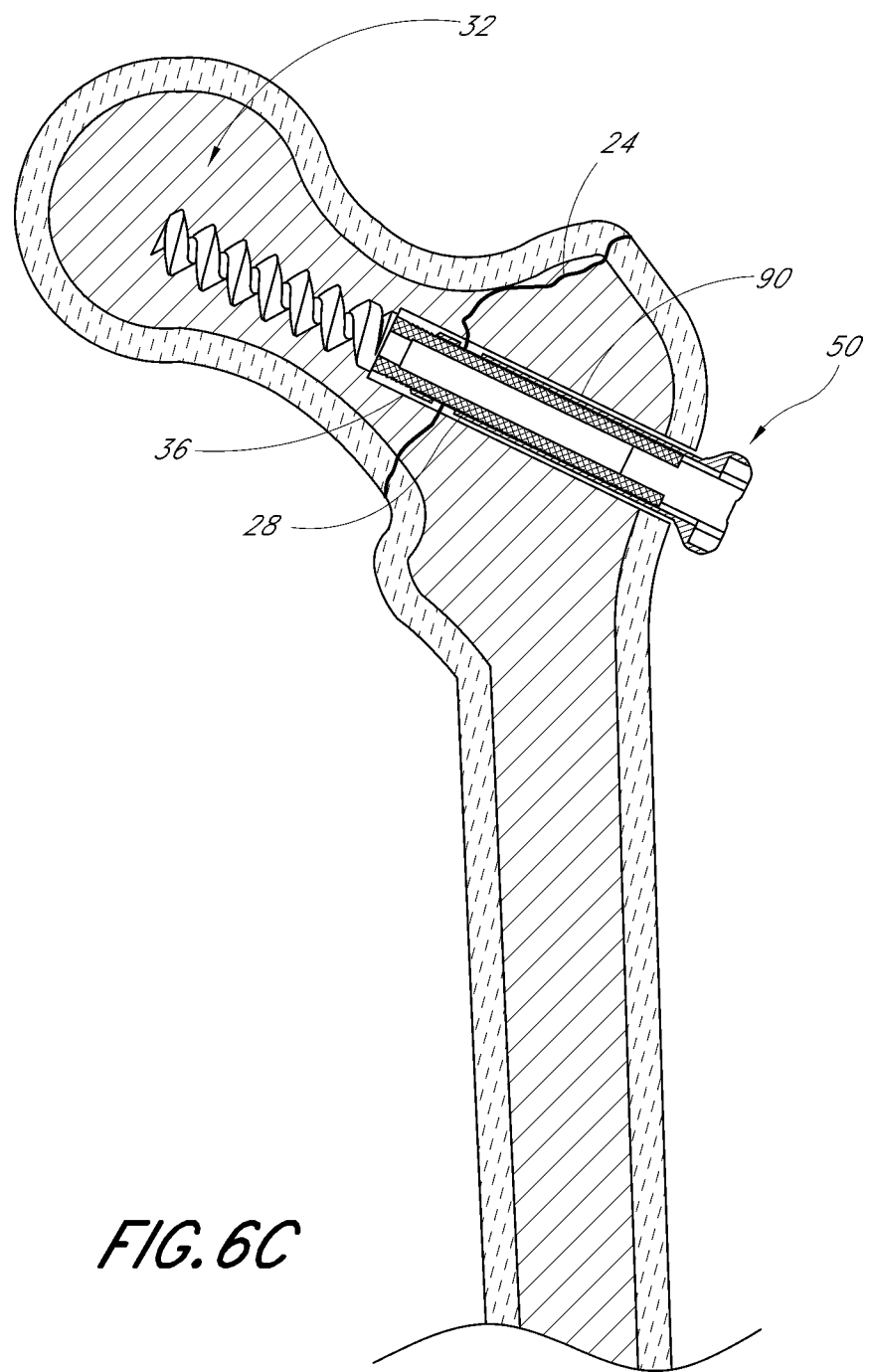

Following appropriate tensioning of the proximal anchor 50, the second portion 38 of the body 28 is preferably detached from the first portion 36 and removed. See FIG. 6C. In the illustrated embodiment, this involves rotating the second portion 38 with respect to the first portion via the coupling 70. In connection with many of the fractures identified previously herein, a single fixation device 12 may be all that is clinically indicated. However, two or three or more fixation devices 12 may be utilized to reduce a single fracture, depending upon the location and physical requirements of the fractured portion of the bone. For example, in the case of proximal femoral fractures of the type illustrated herein, typically at least two and preferably three fixation devices 12 will be implanted to span the femoral neck. The use of three fixation devices 12 desirably provides sufficient compression across the fracture, as well as minimizes the risk of rotation of the head of the femur around the axis of a single fixation device 12. The proximal end of the fixation devices may be connected together such as through a three-holed plate or rod, or may be independent of each other.

Following removal of the second portion 38 of each body 28, the access site may be closed and dressed in accordance with conventional wound closure techniques.

In a modified arrangement, the second portion 38 may form part of the driving device, which is used to rotate the proximal anchor 50 and thus cancellous bone anchor 34 into the head of the femur. The second portion 38 is used to apply proximal traction so as to compress the fracture. After appropriate tensioning, the second portion 38 can be de-coupled from the first portion 36 and removed with the driving device.

In the foregoing variation, the second portion 38 may be connected to a rotatable control such as a thumb wheel on the deployment device. A container may be opened at the clinical site exposing the proximal end of the implant, such that the distal end of the second portion 38 may be removably coupled thereto. Proximal retraction of the hand tool will pull the implant out of its packaging. The implant may then be positioned within the aperture in the bone, rotated to set the distal anchor, and the hand piece may be manipulated to place proximal traction on the second portion 38 while simultaneously distally advancing the proximal anchor. Following appropriate tensioning across the fracture, the second portion 38 may be disengaged from the implant, and removed from the patient. In the example of a threaded engagement, the second portion 38 may be disengaged from the implant by rotating a thumb wheel or other rotational control on the hand piece. In an alternate embodiment, such as where the second portion 38 comprises a pull wire, following appropriate tensioning across the fracture, a first end of the pull wire is released such that the pull wire may be removed from the implant by proximal retraction of the second end which may be attached to the hand piece.

Preferably, the clinician will have access to an array of fixation devices 12, having, for example, different diameters, axial lengths and, if applicable, angular relationships. These may be packaged one per package in sterile envelopes or peelable pouches, or in dispensing cartridges which may each hold a plurality of devices 12. Upon encountering a fracture for which the use of a fixation device is deemed appropriate, the clinician will assess the dimensions and load requirements, and select a fixation device from the array, which meets the desired specifications.

In some instances, a clinician may want to introduce two or more fixation devices 12 into the femoral head 14 to secure the fracture 24. This may be desirable if the clinician determines that, based upon the nature of the fracture 24, there is a possibility that the head 14 of the femur 10 could rotate about a single fixation device 12. Even minor rotation can inhibit the healing of the fracture. Significant rotation can result in failure of the fixation device or necrosis of the femoral head. Two or more fixation devices 12 may also be desirable where the direction of the fracture is generally parallel to the axis of implantation as is understood in the art.

The fixation device 12 of the present invention may also be used in combination with intramedullary nails or rods, as will be understood by those of skill in the art.

Figure 7:
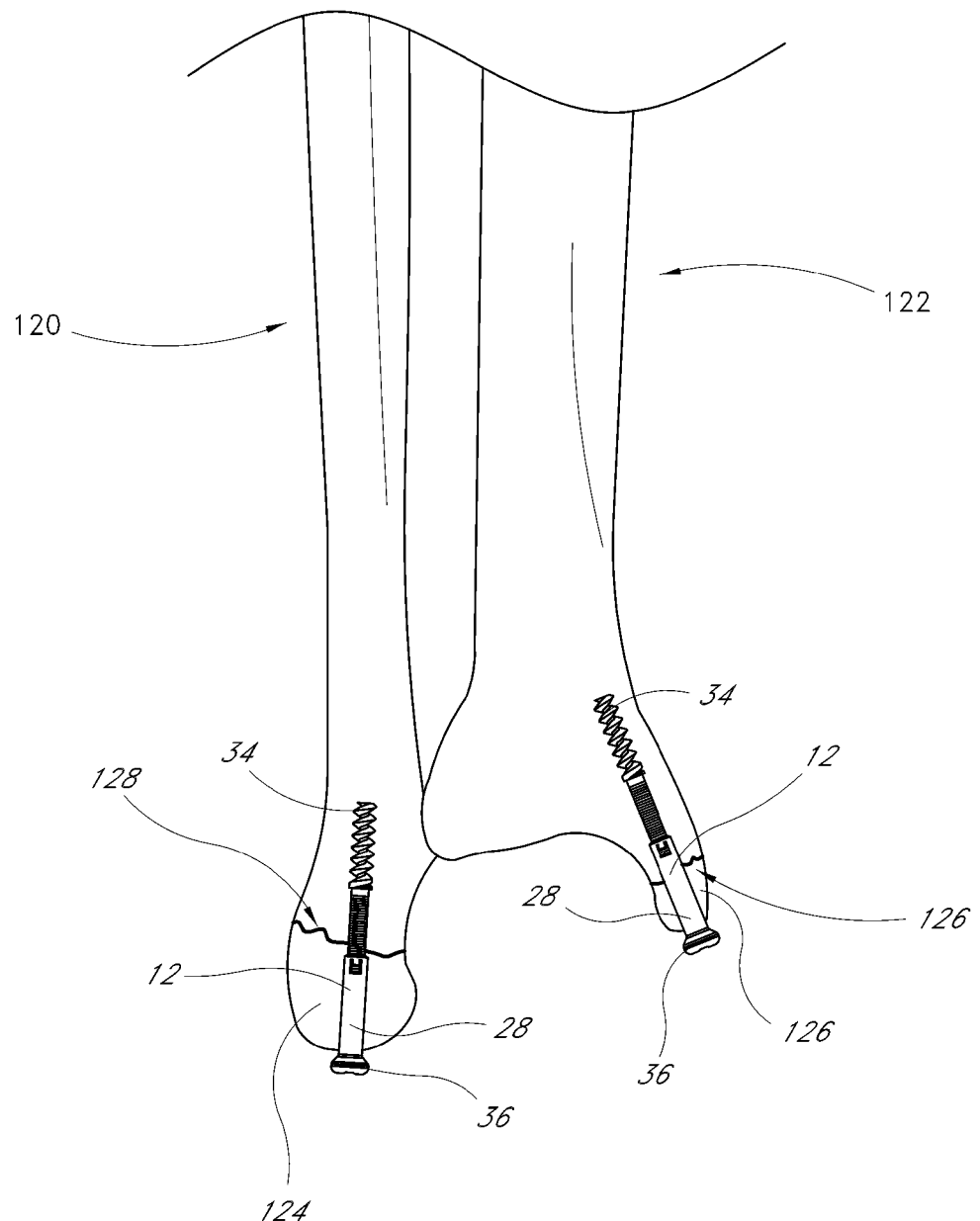
FIG. 7 is an anterior view of the distal tibia and fibula, with fixation devices similar to that of FIG. 1 arranged across lateral and medial malleolar fractures.

The fixation device 12 of the present invention may be used in any of a wide variety of anatomical settings beside the proximal femur, as has been discussed. For example, lateral and medial malleolar fractures can be readily fixed using the device of the present invention. Referring to FIG. 7, there is illustrated an anterior view of the distal fibula 120 and tibia 122. The fibula 120 terminates distally in the lateral malleolus 124, and the tibia 122 terminates distally in the medial malleolus 126.

A fixation device 12 in accordance with the present invention is illustrated in FIG. 7 as extending through the lateral malleolus 124 across the lateral malleolar fracture 128 and into the fibula 120. Fixation device 12 includes a distal anchor 34 for fixation within the fibula 120, an elongate body 28 and a proximal anchor 50 as has been discussed.

FIG. 7 also illustrates a fixation device 12 extending through the medial malleolus 126, across a medial malleolar fracture 130, and into the tibia 122. Although FIG. 7 illustrates fixation of both a lateral malleolar fracture 128 and medial malleolar fracture 130, either fracture can occur without the other as is well understood in the art. Installation of the fixation devices across malleolar fractures is accomplished utilizing the same basic steps discussed above in connection with the fixation of femoral neck fractures.

FIGS. 8, 8A, 8B, and 9 illustrate a modified fixation device 132 that has certain modifications that can be used on any of the embodiments discussed herein. With initial reference to FIG. 8, the proximal anchor 50 includes a plurality of graduations 134 that are positioned on the housing 52. The graduations 134 are visual indicia that are spaced, preferably uniformly, along the longitudinal axis of the proximal anchor 50. Preferably, the graduations 134 are arranged so that they are visible from several orientations of the fixation device 132. In the illustrated embodiment, the graduations extend 360 degrees around the proximal anchor 50 and include one or more gaps 136. The graduations 134 can be formed by a variety of manufacturing methods, e.g., laser etching, chemical etching, and application of bio-compatible paint.

In use, the graduations 134 facilitate the accurate positioning of the fixation device 132. For example, in one embodiment, the clinician inserts an elongated member (e.g., a k-wire) of a known length across the fracture 24 or fusion site. The clinician uses a measuring device, which is preferably calibrated to the length of the elongated member, to measure the length of the proximal portion of the elongated member so as to determine the length of the device required to fix the fracture or joint. In a modified embodiment, the elongated member includes measurement graduations to directly indicate the desired length of the fixation device or a measuring device can be placed directly across the fracture or fusion site. In another modified embodiment, the elongated member can be inserted into a blind hole that has been predrilled to the desired depth of the fixation device.

With the measurement, the clinician can chose an appropriately sized fixation device. By comparing the elongated member to the fixation device, the clinician can note the graduation 134 that most closely corresponds to the desired depth of the fixation device. Using the graduations 134 as a reference, the clinician positions the fixation device 132 at the proper depth. In this manner, when proximal traction is applied to the fixation device and the distal anchor 50 is moved distally, the distal end 32 of the device will not advance.

The graduations 134, therefore, facilitate accurate positioning of the distal end 32 of the fixation device 132. Accurate positioning prevents the distal tip of the fixation device from contacting the distal cortex or penetrating the head of the femur thereby reducing the chances of femoral head cutout, which is common in prior art bone screws. Use of the graduations 134 also reduces the amount of fluoroscopy time that is required to ensure accurate position of the fixation device.

Figure 9:
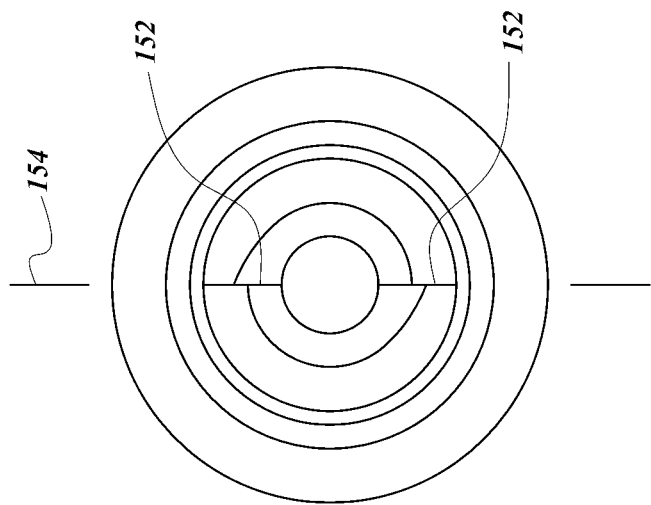
FIG. 9 is a front view of the fixation device of FIG. 8 taken in the direction of arrow A.
Figure 8B:
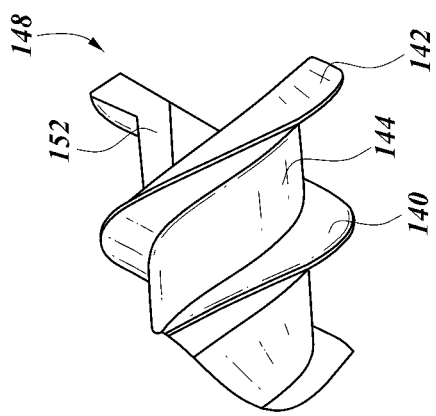
FIG. 8B is a side view of portion of the fixation device illustrated in FIG. 8A.

In the illustrated embodiment, the distal anchor 34 of the fixation device 132 forms a double helix comprising two elongated structures 140, 142 that are spirally wrapped about a central core 144, which, in turn, defines an central lumen 146 (see FIG. 9). The elongated structures 140, 142, are preferably spirally wrapped about the central core from about 2 to about 20 or more revolutions. As with the embodiments described above, the shape, the width, and height of the elongated bodies 140, 142 can be optimized through routine experimentation to optimize the retention force in the bone.

Advantageously, the distal anchor 34 may include a distal cutting tip 148. The distal cutting tip 148 is preferably configured such that the distal anchor 34 is self-drilling and self taping. In the illustrated embodiment, the cutting tip 148 comprises two cutting members 150a, 150b, which are positioned on the distal end of the elongated members 140, 142. The illustrated cutting members 150a, 150b include a first cutting face 152 that defines a plurality of cutting edges as will be described in more detail below. In the illustrated embodiment, the first cutting face 152 lies generally along a centerline 154 (see FIG. 9) that extends through the longitudinal axis of the fixation device. As such, the cutting members 150a, 150b have a neutral cutting angle. However, in one modified embodiment, the cutting face 152 may have a positive rake to produce a more aggressive cut and a looser path in the bone. In another embodiment, the cutting face 152 may have a negative rake angle to produce less aggressive cutting and a tighter cutting path.

Figure 8:
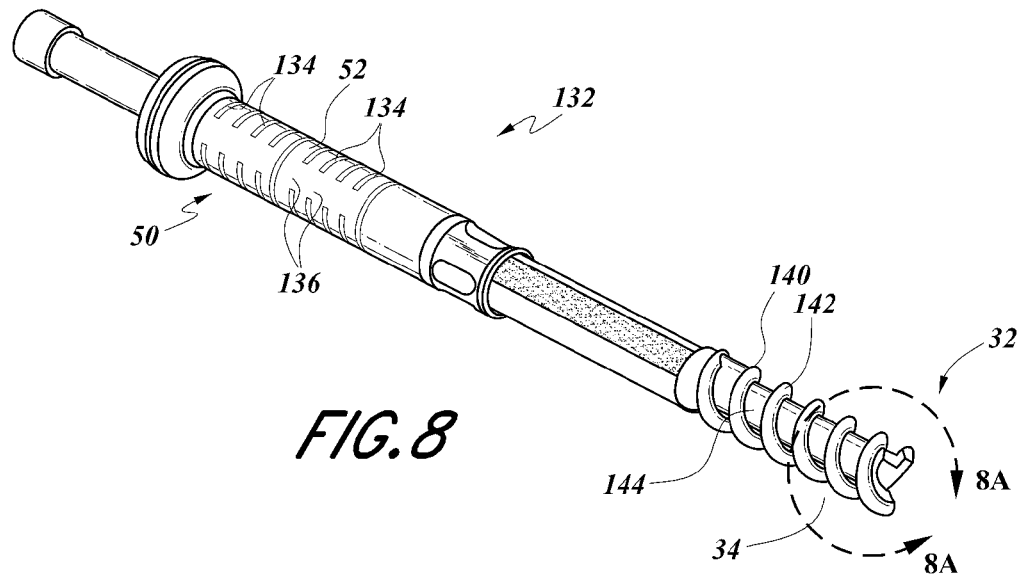
FIG. 8 is a side perspective view of a modified fixation device.
Figure 8A:
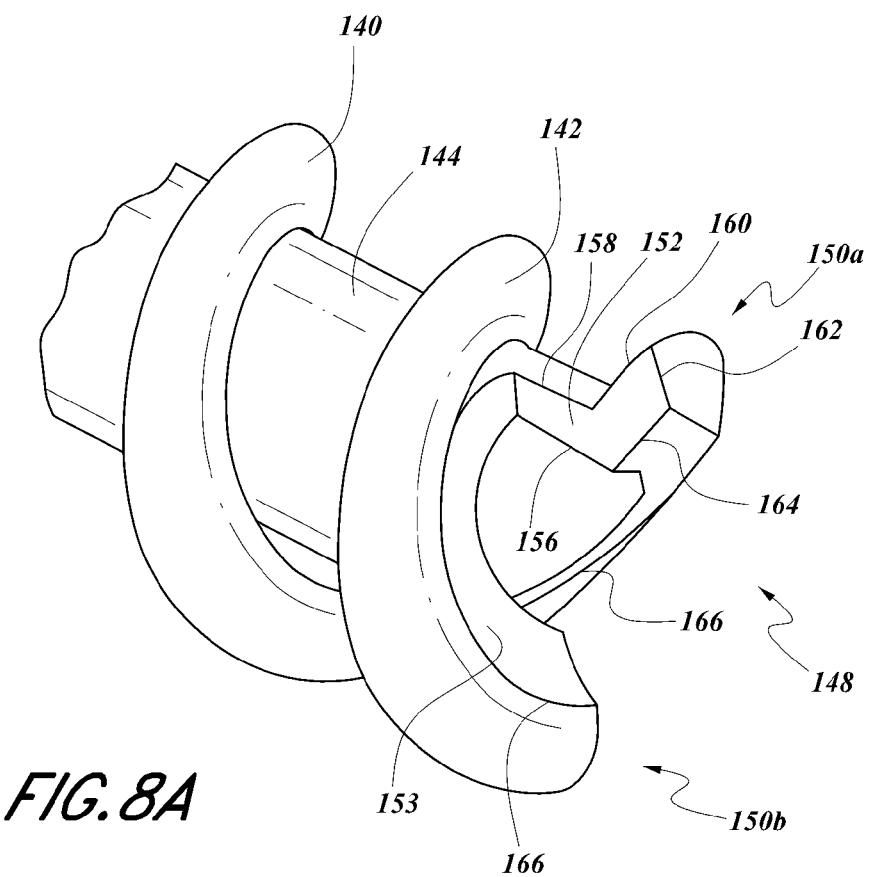
FIG. 8A is an enlarged view of portion 8A of FIG. 8.

As best seen in FIG. 8A, the illustrated cutting tip 148 also includes a second cutting face 153, which cuts through the central core 144 and extends from the first cutting face 152 of the first cutting member 150a to the first cutting face 152 of the second cutting member 150b. The first cutting face 152 defines at least a first cutting edge 156 and a second cutting edge 158. The first and second cutting edges 156, 158 extend generally parallel to the longitudinal axis of the fixation device 132. The first cutting edge 156 extends generally along the outside diameter of the axial lumen 146 while the second cutting edge 158 extends generally along the outside diameter of the central core 144.

A third cutting edge 160 is formed by the intersection of an upper flank of the elongated member 140 with the cutting face 152. In a similar manner, a fourth cutting edge 162 is formed by the intersection of a lower flank of the elongated member 140 with the cutting face 152. Finally, a fifth cutting edge 164 is defined by the intersection of the first cutting face 152 with the second cutting face 153. The second cutting face 153 also defines a cutting edge 166 that generally follows the outside diameter of the central core 144. All of the cutting edges are preferably sharpened to provide a smooth, clean, positive cutting surface. Such a cutting surface reduces mechanical stresses and the production of heat as the fixation device 132 is inserted into the bone. By reducing mechanical stresses, the device 132 is more easily inserted into the bone. By reducing the production of heat, the cutting surface helps to prevent thermal necrosis.

The cutting tip 148 described above has several advantages. For example, the cutting tip 148 cuts a threaded path for the distal anchor 34 as opposed to "rolling" a thread path as is typical in prior art devices. Thread "rolling" produces a threaded path by compressing the bone to conform to the thread of the distal anchor 34. In contrast, thread cutting forms the threaded path by directly cutting the bone tissue. Thread cutting, therefore, tends to generate less heat and less mechanical stresses than thread rolling. Additionally, because the cutting tip 148 is positioned at the distal end of the elongated members 140, 142, the useful threaded length of the fixation device 132 is increased without increasing the length of the fixation device 132.

It should be appreciated that certain features of the cutting tip 148 can also be used with other types distal anchors 34, such as, for example, a distal anchor with a single or triple helical arrangement or the distal anchors described in U.S. patent application Ser. No. 09/822,803, filed Mar. 30, 2001, and co-pending U.S. patent application entitled "DISTAL BONE ANCHORS FOR BONE FIXATION WITH SECONDARY COMPRESSION", filed Nov. 13, 2001.

The fixation devices described above may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful: 1) the blend of poly(p-dioxanone) and a lactide/glycolide copolymer, as disclosed in U.S. Pat. No. 4,646,741 which is incorporated by reference and (2) the glycolide-rich blend of two or more polymers, one polymer being a high lactide content polymer, and the other being a high glycolide content disclosed in U.S. Pat. No. 4,889,119 which is incorporated by reference. Additional bioabsorbable materials are disclosed in copending application Ser. No. 09/558,057 filed Apr. 26, 2000, the disclosure of which is incorporated in its entirety herein by reference.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the invention (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A method of fixing an anchor to a bone, comprising the steps of:
   providing a fixation device having central lumen extending from a proximal end to a distal end of the fixation device along a longitudinal axis and a double helix having a first radially outwardly extending element and a second radially outwardly extending element thereon, each radially outwardly extending element including a first cutting face extending longitudinally, and a second cutting face which extends along the central lumen from the first cutting face of the first radially outwardly extending element to the first cutting face of the second radially outwardly extending element, the first and second cutting faces forming the distal end of the fixation device by extending from an outer surface of the fixation device to the central lumen;
   cutting a helical path into a bone with the distal end; and
   rotating each radially outwardly extending element along the helical path.

2. The method of claim 1, further comprising engaging a plurality of cutting edges of the first cutting faces with bone.

3. The method of claim 1, wherein the first cutting faces have a neutral cutting angle.

4. The method of claim 1, wherein the first cutting faces have a positive rake.

5. The method of claim 1, wherein the first cutting faces have a negative rake.

6. The method of claim 1, wherein at least one cutting edge of the first cutting faces extends generally parallel to the longitudinal axis of the fixation device.

7. The method of claim 1, wherein at least one cutting edge of the first cutting faces extends generally perpendicularly to the longitudinal axis of the fixation device.

* * * * *